United States Patent
Ortmaier

(10) Patent No.: US 8,649,905 B2
(45) Date of Patent: Feb. 11, 2014

(54) MEDICAL WORKSTATION AND OPERATING DEVICE FOR THE MANUAL MOVEMENT OF A ROBOT ARM

(75) Inventor: Tobias Ortmaier, Hemmingen (DE)

(73) Assignee: KUKA Laboratories GmbH, Augsburg (DE)

( * ) Notice: Subject to any disclaimer, the term of this patent is extended or adjusted under 35 U.S.C. 154(b) by 533 days.

(21) Appl. No.: 13/062,637

(22) PCT Filed: Sep. 4, 2009

(86) PCT No.: PCT/EP2009/006454
§ 371 (c)(1),
(2), (4) Date: Mar. 30, 2011

(87) PCT Pub. No.: WO2010/025943
PCT Pub. Date: Mar. 11, 2010

(65) Prior Publication Data
US 2011/0282493 A1 Nov. 17, 2011

(30) Foreign Application Priority Data
Sep. 8, 2008 (DE) .......................... 10 2008 041 867

(51) Int. Cl.
*G05B 19/04* (2006.01)
*G05B 19/18* (2006.01)
*G05B 15/00* (2006.01)
*G05B 19/00* (2006.01)

(52) U.S. Cl.
USPC ........... 700/257; 700/250; 700/253; 700/254; 700/258; 700/260; 700/261; 901/46

(58) Field of Classification Search
None
See application file for complete search history.

(56) References Cited

U.S. PATENT DOCUMENTS

| 4,000,819 A | 1/1977 | Germond et al. |
| 6,665,554 B1 * | 12/2003 | Charles et al. ................. 600/427 |

(Continued)

FOREIGN PATENT DOCUMENTS

| EP | 0 883 376 B1 | 4/2006 |
| WO | 01/18617 A1 | 3/2001 |
| WO | 2007/005367 A2 | 1/2007 |
| WO | 2007/047782 A2 | 4/2007 |

OTHER PUBLICATIONS riviere_cameron_2003_1.pdf (Cameron N. Riviere, Member, Wei Tech Ang,, and Pradeep K. Khosla, Toward Active Tremor Canceling in Handheld Microsurgical Instruments,, Oct. 2003, IEEE Transactions on Robotics and Automation, vol. 19, No. 15, pp. 793-800).*

(Continued)

*Primary Examiner* — Khoi Tran
*Assistant Examiner* — Bao Long T Nguyen
(74) *Attorney, Agent, or Firm* — Wood, Herron & Evans, LLP

(57) ABSTRACT

The invention relates to a medical workstation and an operating device (1) for the manual movement of a robot arm (M1-M3). The operating device (1) comprises a controller (5) and at least one manual mechanical input device (E1-E3) coupled to the controller (5). The controller (5) is designed to generate signals for controlling a movement of at least one robot arm (M1-M3) provided for treating a living being (P) based on a manual movement of the input device (E1-E3) such that the robot arm (M1-M3) carries out a movement corresponding to the manual movement. The input device (E1, E2) comprises at least one mechanical damping unit (27, 40), which generates a force and/or torque during a manual movement of the input device (E1, E2) for at least partially suppressing a partial movement resulting from a tremor of the person operating the input device (E1, E2).

18 Claims, 3 Drawing Sheets

(56) References Cited

U.S. PATENT DOCUMENTS

Figure 1:
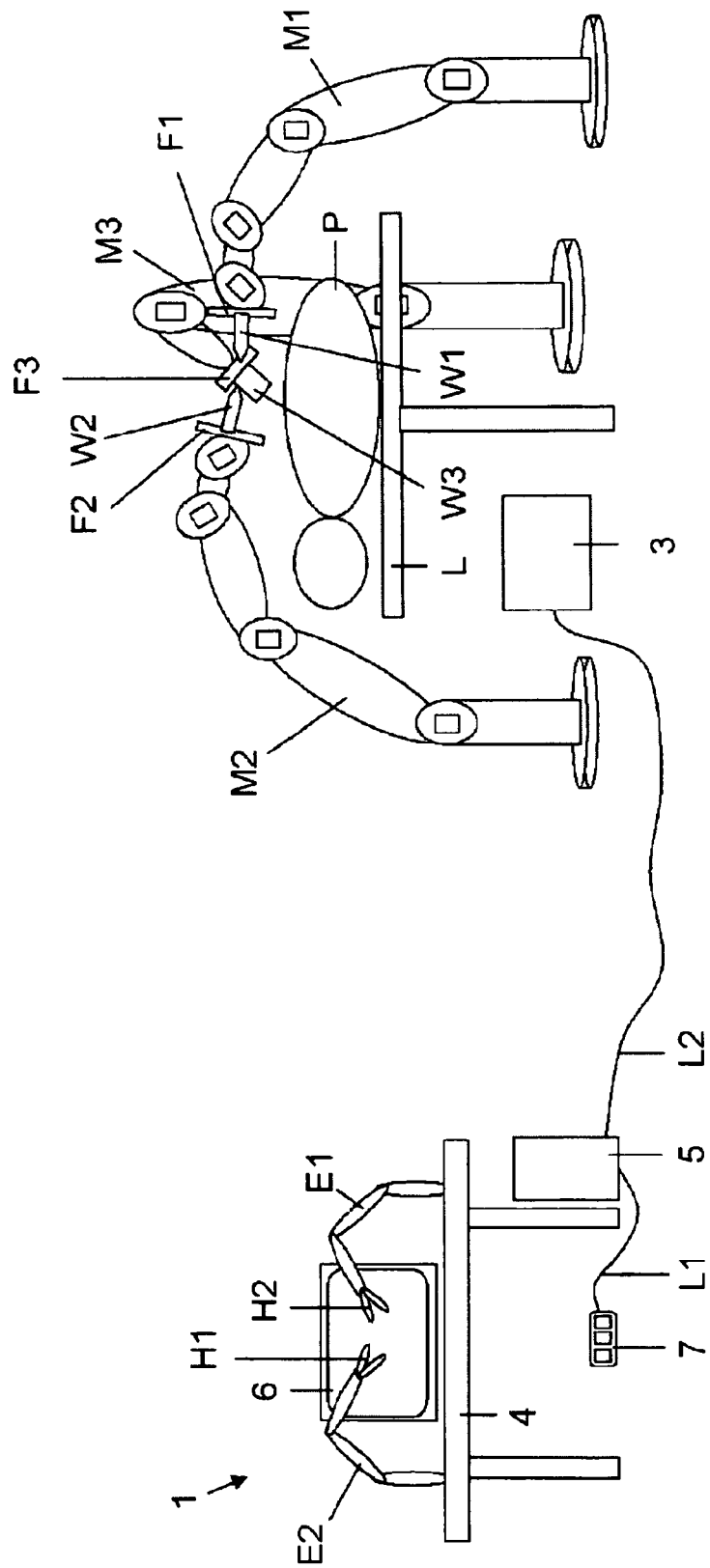

| | | |
|---|---|---|
| 6,723,106 B1 * | 4/2004 | Charles et al. .............. 606/130 |
| 6,994,703 B2 * | 2/2006 | Wang et al. .................. 606/10 |
| 2004/0034302 A1 | 2/2004 | Abovitz et al. |
| 2004/0106916 A1 * | 6/2004 | Quaid et al. ................. 606/1 |
| 2004/0116906 A1 * | 6/2004 | Lipow ......................... 606/1 |
| 2004/0243147 A1 * | 12/2004 | Lipow ......................... 606/130 |
| 2008/0161830 A1 * | 7/2008 | Sutherland et al. ........... 606/130 |
| 2008/0188868 A1 | 8/2008 | Weitzner et al. |
| 2008/0215065 A1 * | 9/2008 | Wang et al. .................. 606/130 |

OTHER PUBLICATIONS riviere_cameron_1998_1.pdf, (Cameron N. Riviere, R. Scott Rader, and Nitish V. Thakor, Adaptive Canceling of Physiological Tremor for Improved Precision in Microsurgery, Jul. 1998 839, IEEE Transactions on Biomedical Engineering, vol. 45, No. 7, pp. 839-846).*

European Patent Office; Search Report in International Patent Application No. PCT/EP2009/006454 mailed Nov. 20, 2009; 6 pages.

* cited by examiner

MEDICAL WORKSTATION AND OPERATING DEVICE FOR THE MANUAL MOVEMENT OF A ROBOT ARM

The invention relates to a medical work station and an operating device for the manual movement of a robot arm.

In telepresence or teleaction, robots are remote controlled over relatively great distances. Intended commands are registered at an operating device or input console by an operator, using sensors, and are processed and transmitted to the remotely located robot. The motion of the robot may possibly be monitored via a visual feedback channel. However, persons in general exhibit a certain trembling, known as tremor, whereby an unwanted shaking motion produced by the tremor becomes superimposed over the desired manual movement of the operating device. The effect is further intensified if the movement at the operating device is scaled up, i.e., the movements of the robot are greater than those of the input station.

EP 0 883 376 B1 discloses a medical work station having a plurality of robot arms provided for treating a patient, which are movable manually using an operating device of the medical work station. The operating device includes a control device, and first and second input devices coupled with the latter. If the input devices are moved, the control device generates a signal to move the robot arms accordingly. The control device also has an analog or digital filter, which filters out of the signal a signal component in the frequency range of 6-12 Hz assigned to a hand tremor of the surgeon operating the operating device.

The object of the invention is to specify an alternative operating device for such a medical workstation, which is relatively insensitive to a tremor of a person operating the operating device.

The object of the invention is satisfied by an operating device for the manual movement of a robot arm, having
- a control device which is set up to generate signals provided to control a motion of at least one robot arm provided for treating a living being, and
- at least one manual mechanical input device coupled with the control device, where the control device generates the signals on the basis of a manual movement of the input device, so that the robot arm executes a movement corresponding to the manual movement, the mechanical device having at least one mechanical damping device which, at a manual movement of the input device, produces a force and/or a torque to at least partially suppress a partial movement resulting from a tremor of the person operating the input device.

The operating device according to the invention is provided to move the robot arm manually over a certain distance. The mechanical damping device may be set up in particular so that when the input device is moved manually it generates a force and/or a torque directed contrary to the manual movement, to at least partially suppress a partial movement resulting from a tremor of the person operating the input device. One possible application for the operating device according to the invention is in the medical environment, in which for example a doctor treats a living being using one or more robot arms. Another aspect of the invention therefore relates to a medical work station that has the operating device according to the invention and at least one robot arm provided for treating the living being, the movement of the robot arm being controllable manually by means of the operating device.

If the operating device according to the invention is employed in the medical environment, then the at least one robot arm may be provided for example with a medical instrument, in particular with a minimally invasive medical instrument, where the doctor moves the robot arm and hence the medical instrument using the manual input device. The robot arm may be moved for example in six degrees of freedom. The input device may have for example the same number of degrees of freedom or more degrees of freedom than the robot arm being moved. A relatively simple manual movement of the robot arm results, based on the manual movement of the robot arm using the input device.

The operating device according to the invention has, in addition to the mechanical input device, the control device coupled with it. Based on the movement of the input device, the control device generates signals by means of which the movement of the robot arm is controlled corresponding to the movement of the input device. The control device may for example activate the robot arms directly, or may be connected to another control device which activates drives to move the robot arms. In the second case, if a plurality of robot arms are used, a single control device may jointly activate all or several of the robot arms directly, or an individual control device which is activated by the control device of the operating device according to the invention may be assigned to each individual robot arm.

The input device is intended to be operated by hand by a person. Due to the so-called tremor of this person, the desired manual movement of the input device is superimposed by a trembling motion caused by the tremor, the resulting partial motion. According to the invention, however, the input device has at least one mechanical damping device, which generates the force or torque that is directed contrary to the manual movement of the input device and is executed in such a way that it at least partially suppresses the partial motion resulting from the tremor of the person operating the input device. The mechanical damping device generates in particular a force or torque dependent on the movement of the input device, which is directed contrary to the partial motion.

The mechanical damping device may have for example a passive viscous damping element, whose damping is assigned in particular to a frequency range assigned to the tremor. That makes it possible in a relatively simple way to focus the force or torque contrary to the trembling motion caused by the tremor, and to at least partially suppress that motion. The magnitude of the damping of the damping element may be constant, or else adjustable, for example in order to be adjusted to a particular person operating the operating device according to the invention. An adjustment of the damping may be made for example via electrorheological fluids. The damping may also be dependent on the speed of the manual movement of the input device and/or dependent on a scaling, so that the degree of movement of the robot arm differs from the degree of movement of the input device by the scaling. In particular, scaling down may be employed in the medical environment, in order to cause the robot arm for example to execute a relatively fine motion, while the person operating the operating device executes a corresponding relatively large-scale motion. In surgery, this is of interest for example in the case of anastomoses.

According to one variant of the operating device according to the invention, the input device has an axis, a lever mounted so that it is rotatable around the axis and/or movable along the axis, and an electric motor which is set up, in the case of a manual movement of the lever along the axis to generate the force on the lever contrary to this manual movement, and/or in the case of a manual movement of the lever around the axis, to generate the torque on the lever contrary to this manual movement. The input device according to this embodiment accordingly has at least one axis, to which the electric motor is assigned. The electric motor may be used, among other things, to execute the operating device under the control of force. According to this variant, the force control is used in particular to intervene selectively in the area in which the trembling motion (partial motion) caused by the tremor occurs, for example by activating or controlling the electric motor so as to apply the force or torque directed contrary to the trembling motion to the lever assigned to the axis. Thus it is possible, in a relatively simple way and with relatively simple means, to compensate at least partially for the trembling motion, in particular if the operating device is executed under force control.

The oppositely directed torque $\tau_{Motor}$ to be applied by the electric motor may be calculated for example according to the following formula:

$$\tau_{Motor} = D \cdot (\theta'_s - \theta')$$

where D is a damping factor which is assigned in particular to the frequency range of the tremor, $\theta'$ is the speed at which the lever turns around the axis, and $\theta'_s$ is the time derivative of a target angle of the lever. If the target angle does not change, or changes only relatively slowly, then $\theta'_s$ becomes zero, or possibly may be ignored. The damping factor may be constant, or may for example be dependent on the speed at which the lever turns around the axis. The magnitude of the damping of the damping element may also be adjustable, for example in order to be matched to a particular person operating the operating device according to the invention. The damping may also be dependent on a scaling, where the degree of movement of the robot arm differs from the degree of movement of the input device by the scaling.

According to other embodiments of the operating device according to the invention, the oppositely directed torque $\tau_{Motor}$ to be applied by the electric motor may be calculated according to one of the following formulas.

$$\tau_{Motor} = D \cdot (\theta'_s - \theta') + k \cdot (\theta_s - \theta)$$

$$\tau_{Motor} = D \cdot (\theta'_s - \theta') + m \cdot (\theta''_s - \theta'')$$

$$\tau_{Motor} = D \cdot (\theta'_s - \theta') + k \cdot (\theta_s - \theta) + m \cdot (\theta''_s - \theta'')$$

where k is a virtual rigidity assigned to the lever, m is a virtual mass or inertia assigned to the lever, $\theta_s$ is a target angle of the lever relative to the axis, $\theta$ is a (target) angle by which the lever is turned around the axis relative to the target angle $\theta_s$, $\theta''$ is the acceleration with which the lever turns around the axis, and $\theta'_s$ is the time derivative of the target angle of the lever. If the target angle does not change, or changes only relatively slowly, then $\theta'_s$ and $\theta''_s$ become zero, or possibly may be ignored.

The speed may be ascertained for example by means of position signals assigned to the lever. When choosing the damping factor, and if applicable the virtual rigidity and the virtual mass/virtual inertia, allowance may be made for a latency which occurs due to the calculation of the speed by means of the position signals. However, the speed may also be ascertained by means of a speed sensor assigned to the lever or the axis.

Figure 2:
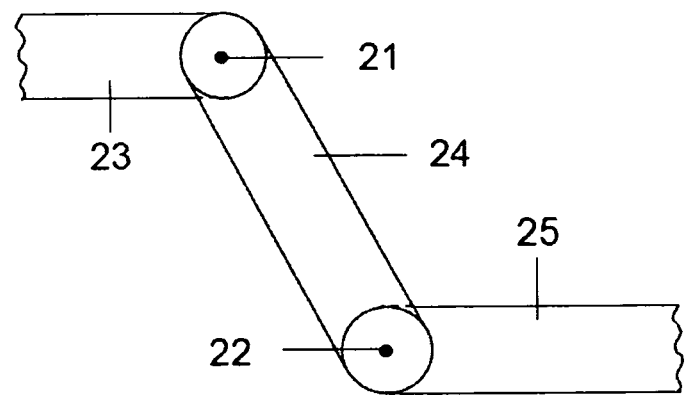
Figure 3:
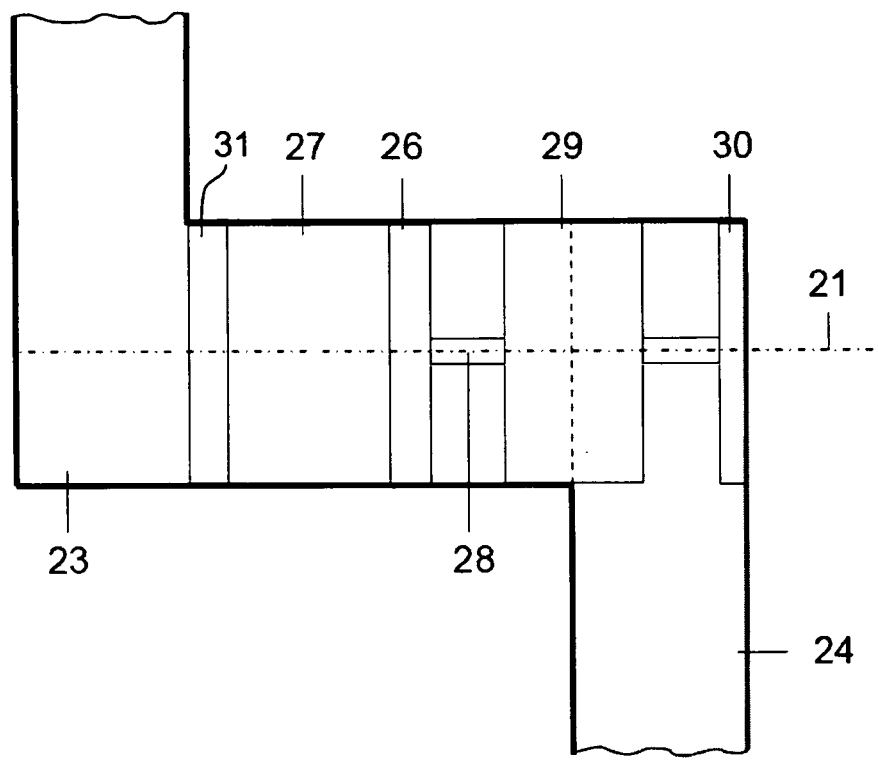
Figure 4:
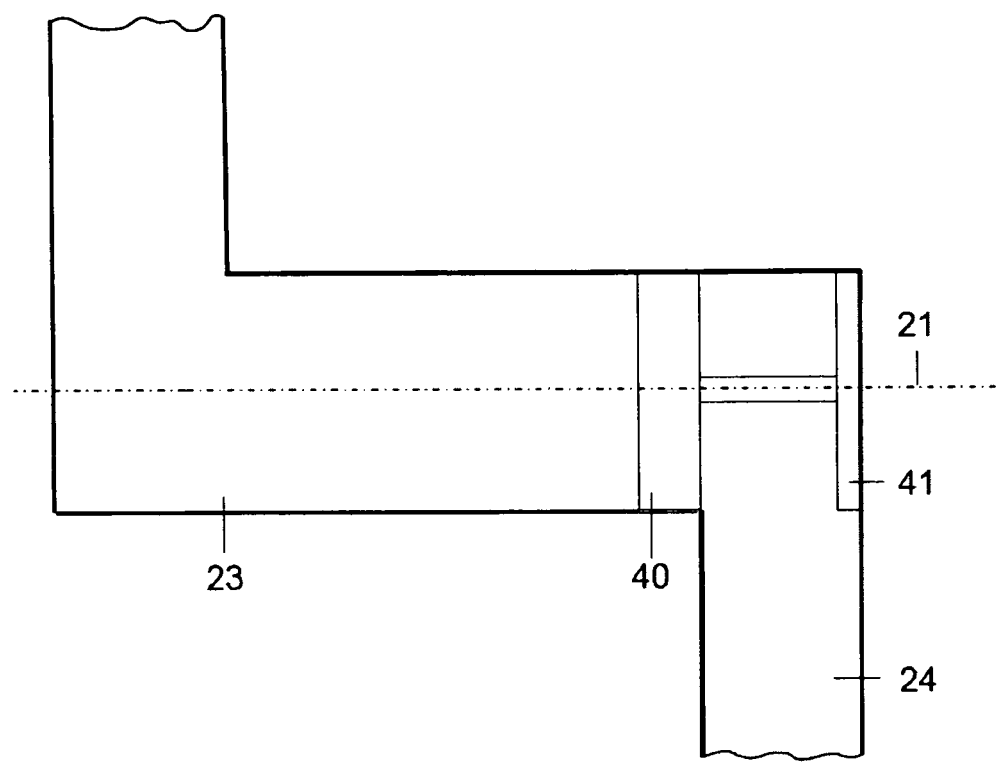

Examples of exemplary embodiments of the invention are depicted in the accompanying schematic drawing. The figures show the following:

FIG. 1 a medical work station with a plurality of robot arms and an operating device having mechanical manual input devices for moving the robot arms manually, and FIGS. 2 and 3 detail views of one of the mechanical manual input devices, and FIG. 4 a detail view of an alternative mechanical manual input device for the operating device.

FIG. 1 shows a medical work station which has a patient table L, a plurality of robot arms M1-M3 and an operating device 1 for moving robot arms M1-M3 manually. Each of the robot arms M1-M3 has a plurality of axes that are movable by means of drives and an attaching device F1-F3, and is movable for example with reference to six degrees of freedom.

In the case of the present exemplary embodiment, lying on patient table L is a person P, who may be treated by means of robot arms M1-M3, or by means of instruments attached to the attaching devices F1-F3 of robot arms M1-M3. Attached to each of the attaching devices F1, F2 of robot arms M1, M2 are for example medical instruments W1, W2, and attached to the attaching device F3 of robot arm M3 is for example a camera W3.

In the case of the present exemplary embodiment, the drives of robot arms M1-M3, medical instruments W1, W2 and camera W3 are connected to a first control computer 3 in a manner not shown. Running on first control computer 3 is a computer program by means of which control computer 3 is able to activate the drives of robot arms M1-M3 in such a way that the axes of robot arms M1-M3 move in a desired manner, so that the attaching devices F1-F3 or the tool center points of medical instruments W1, W2 and of camera W3 assume a desired location (position and orientation).

The medical work station also includes operating device 1. In the case of the present exemplary embodiment, the latter has a second control computer 5, two manual input devices E1, E2 situated on a table 4 and connected to second control computer 5 in a manner not shown, a display screen connected to second control computer in a manner not shown, and a foot-operated switchover device 7 connected to second control computer 5 by means of a cable L1. In addition, the two control computers 3, 5 are able to communicate with each other via a data line L2.

A part of one of the two manual input devices E1, E2, for example manual input device E1, is depicted in FIGS. 2 and 3.

In the case of the present exemplary embodiment, the two manual input devices E1, E2 each have a handgrip H1, H2, a plurality of axes 21, 22 and a plurality of levers 23-25. In the detail view of manual input device E1 shown in FIG. 2, lever 24 is shown rotatable around axis 21 relative to lever 23 and lever 25 is shown rotatable around axis 22 relative to lever 24.

A doctor, not shown in further detail in the figures, is able to move manual input devices E1, E2 manually with reference to at least six degrees of freedom, using handgrips H1, H2. Manual input devices E1, E2 have for example angle sensors 26 assigned to the respective axes 21, 22 of manual input devices E1, E2 and depicted in FIG. 3, whose signals are conveyed to second control computer 5. Running on second control computer 5 in turn is a computer program that recognizes movements of manual input devices E1, E2 on the basis of the signals originating from manual input devices E1, E2. The two manual input devices E1, E2 may also have more than six degrees of freedom.

In the case of the present exemplary embodiment, manual input device E1 is provided to move robot arm M1. When manual input device E1 is moved manually by means of its handgrip H1, angle sensors 26 of manual input device E1 detect angular changes of the relevant axes 21, 22. From the signals generated by angle sensors 26, second control computer 5 ascertains corresponding movements of manual input device E1 and transmits via cable L2 a corresponding notification to first control computer 3, which thereupon activates the drives of robot arm M1 in such a way that its attaching device F1 or the tool center point of medical instrument W1 executes a movement corresponding to the manual movement of manual input device E1.

In the case of the present exemplary embodiment, manual input device E2 is provided to move the two other robot arms M2, M3. In order to select one of the two robot arms M2, M3 for the movement, the doctor may operate the foot-operated switchover device 7, which is connected by control cable L1 to second control computer 5.

In the case of the present exemplary embodiment, camera W3, with which pictures of the operation situs may be taken, is attached to robot arm M3, so that the doctor obtains for example optical feedback about the locations of robot arms M1, M2 and/or of medical instruments W1, W2. The image data records assigned to the pictures taken with camera W3 are transmitted via cable L2 from first control computer 3 to second control computer 5, so that second control computer 5 is able to display these images on screen 6.

Persons normally exhibit a natural trembling motion, the so-called tremor. Because of the tremor, a desired movement of the doctor when moving manual input devices E1, E2 has a partial motion assigned to the trembling motion superimposed upon it. In order to at least partially suppress the latter, manual input devices E1, E2 include damping devices.

In the case of the present exemplary embodiment, an electric motor 27 is assigned for example to axis 21 or to lever 24, which, as shown in greater detail in FIG. 3, is mounted by means of a bearing 30 so that it is rotatable with reference to axis 21 relative to lever 23; said electric motor is coupled to a transmission 29 by means of its shaft 28. Electric motor 27 also has for example a brake 31. Electric motor 27, brake 31 and angle sensor 26 are connected to second control computer 5 in a manner not shown. Electric motors may also be assigned to the other axes of manual input devices E1, E2.

By means of electric motor 27, a force or a torque $\tau_{Motor}$ may be applied to lever 24. Running on second control computer 5 is not only a computer program that generates the signals for moving robot arms M1-M3 on the basis of the signals coming from angle sensors 26, but also a computer program that activates or controls electric motor 27 in such a way that it produces a torque $\tau_{Motor}$ contrary to the trembling motion of the doctor operating operating device 1. The trembling motion superimposed on the desired movement of lever 24 is thereby damped, whereby signal components of the signals coming from angle sensors 26 caused by the trembling motion of the doctor are at least reduced.

In the case of the present exemplary embodiment, second control computer 5 calculates the torque $\tau_{Motor}$ to be applied by electric motor 27 according to the following equation:

$$\tau_{Motor}=D\cdot(\theta'_s-\theta')$$

where D is a damping factor, $\theta'$ is the speed at which lever 24 turns around axis 21, and $\theta'_s$ is the time derivative of a target angle of lever 24. If the target angle does not change, or changes only relatively slowly, then $\theta'_s$ becomes zero, or possibly may be ignored.

The speed at which lever 24 turns around axis 21 due to the manual movement is calculated in the case of the present exemplary embodiment by second control computer 5 from the signals coming from angle sensor 26. Other methods for ascertaining this speed, such as for example a direct measurement using a speed sensor, are also possible.

The damping factor may be constant, but in the case of the present exemplary embodiment is dependent on the speed at which lever 24 is turned around axis 21, dependent on a scaling, and/or dependent on the person who is operating operating device 1. In the event of scaling, the degree of movement of robot arm M1-M3 differs from the degree of movement of manual input device E1, E2 by the scaling.

Second control computer 5 may also calculate the torque $\tau_{motor}$ for electric motor 27 according to one of the following formulas:

$$\tau_{Motor}=D\cdot(\theta'_s-\theta')+k\,(\theta_s-\theta)$$

$$\tau_{Motor}=D\cdot(\theta'_s-\theta')+m\cdot(\theta''_s-\theta'')$$

$$\tau_{Motor}=D\cdot(\theta'_s-\theta')+k\,(\theta_s-\theta)+m\cdot(\theta''_s-\theta'')$$

where k is a virtual rigidity assigned to lever 24, m is a virtual mass or inertia assigned to lever 24, $\theta_s$ is a target angle of lever 24 with reference to axis 21, $\theta$ is the angle by which lever 24 is rotated with reference to target angle $\theta_s$ around axis 21, and $\theta''$ is the acceleration with which lever 24 turns around axis 21.

In the case of the exemplary embodiment shown in FIGS. 2 and 3, lever 24 is mounted so that it can rotate around axis 21. It is also possible, however, that manual input devices E1, E2 have one or more levers which are mounted so that they can move along an axis. If the mounting of lever 24 for example is designed so that it is movable along axis 21, then motor 27 can damp a linear motion of lever 24 along axis 21 in such a way that the partial motion produced by the trembling movement of the doctor is at least partially suppressed.

FIG. 4 shows an additional exemplary embodiment of a damping device for manual input devices E1, E2, which may be used in addition to or alternatively to the damping device designed in the form of electric motor 27.

The damping device shown in FIG. 4 is a viscous damping element 40, which is attached to lever 24 by means of a bearing 41, and damps a movement of lever 24 around axis 21 in particular in a frequency range assigned to the tremor of the doctor.

The damping factor of damping element 40 may be constant, but in the case of the present exemplary embodiment is dependent on the speed at which lever 24 is turned around axis 21, dependent on a scaling, and/or dependent on the person who is operating operating device 1.

In the case of the exemplary embodiment shown in FIG. 4, lever 24 is mounted so that it can rotate around axis 21. It is also possible, however, that manual input devices E1, E2 have one or more levers which are mounted so that they can move along an axis. If the mounting of lever 24 for example is designed so that is movable along axis 21, then damping element 40 can damp a linear motion of lever 24 along axis 21 in such a way that the partial motion produced by the trembling movement of the doctor is at least partially suppressed.

The invention claimed is:

1. An operating device for the manual movement of a robot arm, the operating device comprising:
   at least one manual mechanical input device; and
   a control device coupled with the mechanical input device and generating signals in response to manual movement of the mechanical input device by a user such that the robot arm executes a movement corresponding to the manual movement of the mechanical input device;
   the manual mechanical input device including a mechanical damping device producing at least one of a force or torque that at least partially suppresses a partial movement of the manual mechanical input device resulting from a tremor of the user.

2. The operating device of claim 1, wherein the mechanical damping device comprises a passive viscous damping element.

3. The operating device of claim 2, wherein the passive viscous damping element has an adjustable damping assigned to a frequency range corresponding to the tremor and based on a speed of the manual movement of the input device.

4. The operating device of claim 2, wherein the damping is further based on a scaling factor such that the degree of movement of the robot arm differs from the degree of movement of the input device by the scaling factor.

5. The operating device of claim 1, wherein the mechanical damping device comprises a passive viscous damping element having an adjustable damping assigned to a frequency range corresponding to the tremor and based on a scaling factor such that the degree of movement of the robot arm differs from the degree of movement of the input device by the scaling factor.

6. The operating device of claim 1, wherein the manual mechanical input device comprises:
    a lever mounted for at least one of translation along an axis, or for rotation about the axis; and
    an electric motor operatively coupled with the lever and generating at least one of:
        a force on the lever in response to manual movement of the lever along the axis such that the force resists the movement along the axis, or
        a torque on the lever in response to manual movement of the lever around the axis such that the torque resists the movement around the axis.

7. The operating device of claim 6, wherein the torque applied by the electric motor is determined from:

$$\tau_{Motor} = D \cdot (\theta'_s - \theta')$$

wherein:
    D is a damping factor,
    $\theta'$ is the speed at which the lever rotates around the axis, and
    $\theta'_s$ is the time derivative of a target angle of the lever.

8. The operating device of claim 7, wherein the damping factor (D) is assigned to the frequency range associated with the user tremor.

9. The operating device of claim 7, wherein the damping factor depends on the speed at which the lever turns around the axis.

10. The operating device of claim 6, wherein torque applied by the electric motor is determined from:

$$\tau_{Motor} = D \cdot (\theta'_s - \theta') + k(\theta_s - \theta)$$

wherein:
    D is a damping factor,
    k is a virtual rigidity assigned to the lever,
    $\theta$ is the angle that the lever is turned around the axis relative to the target angle,
    $\theta_s$ is the target angle for the lever relative to the axis,
    $\theta'$ is the speed at which the lever rotates around the axis, and
    $\theta'_s$ is the time derivative of a target angle of the lever.

11. The operating device of claim 10, wherein the damping factor (D) is assigned to the frequency range associated with the user tremor.

12. The operating device of claim 6, wherein torque applied by the electric motor is determined from:

$$\tau_{Motor} = D \cdot (\theta'_s - \theta') + m \cdot (\theta''_s - \theta'')$$

wherein:
    D is a damping factor assigned to the frequency range associated with the user tremor,
    m is a virtual mass or inertia assigned to the lever,
    $\theta'$ is the speed at which the lever rotates around the axis,
    $\theta'_s$ is the time derivative of a target angle of the lever,
    $\theta''$ is the angular acceleration of the lever, and
    $\theta''_s$ is the second time derivative of the target angle of the lever.

13. The operating device of claim 6, wherein torque applied by the electric motor is determined from:

$$\tau_{Motor} = D \cdot (\theta'_s - \theta') + k(\theta_s - \theta) + m \cdot (\theta''_s - \theta'')$$

wherein:
    D is a damping factor,
    k is a virtual rigidity assigned to the lever,
    m is a virtual mass or inertia assigned to the lever,
    $\theta$ is the angle that the lever is turned around the axis relative to the target angle,
    $\theta_s$ is the target angle for the lever relative to the axis,
    $\theta'$ is the speed at which the lever rotates around the axis,
    $\theta'_s$ is the time derivative of a target angle of the lever,
    $\theta''$ is the angular acceleration of the lever around the axis, and
    $\theta''_s$ is the second time derivative of the target angle of the lever.

14. The operating device of claim 13, wherein the damping factor (D) is assigned to the frequency range associated with the user tremor.

15. The operating device of claim 10, wherein the damping factor depends on the speed at which the lever turns around the axis.

16. The operating device of claim 12, wherein the damping factor depends on the speed at which the lever turns around the axis.

17. The operating device of claim 13, wherein the damping factor depends on the speed at which the lever turns around the axis.

18. A medical work station comprising:
    at least one medical robot arm for treating a living being; and
    an operating device for controlling manual movement of the at least one robot arm, the operating device comprising:
        at least one manual mechanical input device,
        a control device coupled with the mechanical input device and generating signals in response to manual movement of the mechanical input device by a user such that the robot arm executes a movement corresponding to the manual movement of the mechanical input device, and
        a mechanical damping device associated with the manual mechanical input device and producing at least one of a force or torque that at least partially suppresses a partial movement of the manual mechanical input device resulting from a tremor of the user.

* * * * *